(12) United States Patent
Baughman et al.

(10) Patent No.: US 10,485,482 B2
(45) Date of Patent: Nov. 26, 2019

(54) CARBON NANO TUBE BASED ANTENNAS

(71) Applicant: Board of Regents, The University of Texas System, Austin, TX (US)

(72) Inventors: Ray Baughman, Dallas, TX (US); Raquel Robles, Schase, TX (US); Mario Romero-Ortega, Coppell, TX (US); Aswini Kanneganti, Arlington, TX (US); Young-tae Kim, Arlington, TX (US); Ryan Landrith, Duncanville, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 634 days.

(21) Appl. No.: 15/116,057

(22) PCT Filed: Feb. 4, 2015

(86) PCT No.: PCT/US2015/014527
§ 371 (c)(1),
(2) Date: Aug. 2, 2016

(87) PCT Pub. No.: WO2015/120102
PCT Pub. Date: Aug. 13, 2015

(65) Prior Publication Data
US 2017/0165471 A1    Jun. 15, 2017

Related U.S. Application Data

(60) Provisional application No. 61/935,379, filed on Feb. 4, 2014.

(51) Int. Cl.
*A61B 5/00* (2006.01)
*A61B 5/04* (2006.01)
(Continued)

(52) U.S. Cl.
CPC .......... *A61B 5/685* (2013.01); *A61B 5/04001* (2013.01); *A61B 5/0478* (2013.01);
(Continued)

(58) Field of Classification Search
CPC . A61B 5/04001; A61B 5/6846; A61B 5/6847; A61B 5/6848; A61B 5/6849;
(Continued)

(56) References Cited

U.S. PATENT DOCUMENTS 7,417,589 B2    8/2008   Sullivan et al.
7,452,452 B2   11/2008   Ren et al.
(Continued)

OTHER PUBLICATIONS

Lin, C.M., Lee, Y.T., Yeh, S.R., Fang, W. (2009), Flexible carbon nanotubes electrode for neural recording, Biosensors and Bioelectronics, vol. 24, Issue 9, pp. 2781-2797. (Year: 2009).*
(Continued)

*Primary Examiner* — Eun Hwa Kim
(74) *Attorney, Agent, or Firm* — FisherBroyles LLP; Anthony Dovale (57) ABSTRACT

A carbon nanotube (CNT) based electrode and method of making the same is disclosed. The CNT based electrode can have a microelectrode made substantially from a substantially inert metal, a first CNT sheet and a second CNT sheet, wherein the first and second CNT sheets are embedded in a collagen film.

20 Claims, 5 Drawing Sheets

(51) Int. Cl.
*B82Y 30/00* (2011.01)
*A61B 5/0478* (2006.01)
*A61N 1/05* (2006.01)
*A61N 1/04* (2006.01)
*B82Y 5/00* (2011.01)

(52) U.S. Cl.
CPC .......... *A61B 5/6847* (2013.01); *A61B 5/6849* (2013.01); *A61N 1/0456* (2013.01); *A61N 1/05* (2013.01); *A61N 1/0529* (2013.01); *B82Y 30/00* (2013.01); *A61B 2562/0285* (2013.01); *A61B 2562/125* (2013.01); *B82Y 5/00* (2013.01); *Y10S 977/742* (2013.01); *Y10S 977/753* (2013.01); *Y10S 977/925* (2013.01)

(58) Field of Classification Search
CPC ............ A61B 5/685; A61B 2562/0285; A61B 2562/125; B82Y 30/00; B82Y 5/00; Y10S 977/753; Y10S 977/742; Y10S 977/925
See application file for complete search history.

(56) References Cited

U.S. PATENT DOCUMENTS

| | | | |
|---|---|---|---|
| 7,938,996 B2 | 5/2011 | Baughman et al. | |
| 7,955,535 B2 | 6/2011 | Liang et al. | |
| 7,988,893 B2 | 8/2011 | Liao et al. | |
| 7,994,477 B2 | 8/2011 | Hung | |
| 8,193,692 B2 | 6/2012 | Lee et al. | |
| 8,204,407 B2 | 6/2012 | Zona et al. | |
| 8,313,820 B2 | 11/2012 | Hung | |
| 8,399,279 B2 | 3/2013 | Lim et al. | |
| 9,731,118 B2 | 8/2017 | Galvan-Garcia | |
| 2008/0183244 A1* | 7/2008 | Greenberg | A61N 1/36046 607/54 |
| 2010/0047317 A1 | 2/2010 | Weber et al. | |
| 2013/0130230 A1 | 5/2013 | Nishizawa et al. | |
| 2013/0320273 A1* | 12/2013 | Kotov | A61N 1/05 252/511 |
| 2014/0288458 A1* | 9/2014 | Yoon | A61N 1/0529 600/547 |

OTHER PUBLICATIONS

Yoon, Inho, et al. "Intracellular Neural Recording with Pure Carbon Nanotube Probes." PLOS ONE 8.6 (2013): e65715.

Mao, Hongli, Naoki Kawazoe, and Guoping Chen. "Uptake and intracellular distribution of collagen-functionalized single-walled carbon nanotubes." Biomaterials 34.10 (2013): 2472-2479.

Carbon Nanotube-based Implantable Electrodes for Neural Engineering Applications, http://flintbox.com/public/project/23520/.

Katz, D., et al. "Carbon nanotubes bridges spanning across metal electrode tips." Journal of Nanoscience and Nanotechnology 8.9 (2008): 4382-4386.

Lin et al. Flexible carbon nanotubes electrode for neural recording.* Biosensors and Bioelectronics, pp. 2791-2797, Feb. 20, 2009 (Feb. 20, 2009), p. 2792; Fig 1a,3 [online] <URL: http://mdl.pme.nthu.edu.tw/NTHU_PME_lab_ENG/papers/88.pdf>.

International Search Report and Written Opinion issued for International Application No. PCT/US15/14527 dated May 29, 2015.

* cited by examiner

CURRENT TECHNOLOGY LIMITATIONS

PROPOSED DESIGN

FIG. 2A

FIG. 2D
NO AGGREGATION OF THE CNT YARNS

CNT-SHEET EMBEDDED ON COLLAGEN FILM

FIG. 2C
NO AGGREGATION OF THE CNT YARNS

CNT-SHEET WITHOUT COLLAGEN
10μm

FIG. 2B
AGGREGATION OF THE CNT YARNS

CNT - SHEETS APPLICATION

PROTOTYPE FABRICATION

CARBON NANO TUBE BASED ANTENNAS

FIELD OF THE INVENTION

This invention relates electrodes for use with medical devices, and more particularly to carbon nanotube sheets based electrodes.

BACKGROUND OF THE INVENTION

The global medical device electrode market which includes primarily ECG (Electrocardiogram), EEG (Electroenchephalogram), EMG (Electromyogram), EOG (Electrooculogram), ENG (Dectroneurogram), TENS (Transcutaneous electrical nerve stimulation) and DBS (Deep brain stimulation) among others, is a highly mature, price sensitive and competitive industry. Current technology limits the effective electrode-tissue interface to enhance sensitivity towards recording and stimulation capabilities for both acute and chronic bio-signal acquisition. The sensitivity and signal to noise ratio (SNR) of neural recordings and the rate of current discharge of the electrode can and should be improved.

Various medical treatments involving electrical stimulation of neural tissue have been used for years and the breadth of treatments is expanding. Prior art electrodes are generally based on inert metals, limiting the capacity of the electrodes. For example, single Pt electrodes have capacities of approximately 300-350 mC/cm$^2$. In order to increase the sensitivity of the electrode and record from a single neuron, the size of the electrode would most likely have to be in the micrometer range. However, as the size of the electrode is decreased, the impedance increases, resulting in poor signal to noise ratio.

Polymer coated electrodes have lower impedance, however the polymers are often fragile and have weak adhesion to the electrode substrate. What is needed is a highly conductive, low impedance, durable electrode that has high biocompatibility.

SUMMARY

Presented herein is a CNT based electrode and method of making the same. In one exemplified aspect, the CNT based electrode comprises a microelectrode comprising a substantially inert metal, a first CNT sheet and a second CNT sheet, wherein the first and second CNT sheets are embedded in a collagen film. In another aspect, at least a portion of the exposed microelectrode is sandwiched between a pair of CNT sheets embedded on collagen film, creating a CNT flag. In still another aspect, after implantation, the CNT flag extends beyond the scar tissue area to reliably pick up neuronal activities.

Related methods of operation are also provided. Other apparatuses, methods, systems, features, and advantages of the carbon nanotube sheets based electrode system and the method of its use will be or become apparent to one with skill in the art upon examination of the following figures and detailed description. It is intended that all such additional apparatuses, methods, systems, features, and advantages be included within this description, be within the scope of the carbon nanotube sheets based electrode system and the method of its use, and be protected by the accompanying claims.

DESCRIPTION OF THE FIGURES

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

DESCRIPTION OF THE INVENTION

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "plate" includes aspects having two or more plates unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The term "substantially," as used herein, may be applied to modify any quantitative representation which could permissibly vary without resulting in a change in the basic function to which it is related.

As used herein, the terms "optional" or "optionally" mean that the subsequently described event or circumstance may or may not occur, and that the description includes instances where said event or circumstance occurs and instances where it does not.

Terms used herein, such as "exemplary" or "exemplified," are not meant to show preference, but rather to explain that the aspect discussed thereafter is merely one example of the aspect presented.

Presented herein is an apparatus and method relating to medical treatments involving electrical stimulation of neural tissue. Prior studies have shown that coating metal electrodes with carbon nanotubes (CNT) dramatically increased the electrode surface due to the large surface area of the carbon nanotubes. This advance reduced the impedance greatly. In fact, in one study, coating the metal electrodes with CNT reduced their impedance by 23 fold, reduced noise levels by 63%, and increased the charge transfer limit by 45 fold. However, it was found that both bare and surface modified electrodes elicited host immune response upon implantation and, thus, fail over time due to the formation of scar tissue around the exposed tip. As is known, scar tissue substantially inhibits the ion distribution between the electrode and the surrounding tissue, which eventually leads to significantly reduced electrical contact with the enclosing tissue. Other issues found in prior studies include delamination of surface modification materials over time, severely reducing or eliminating the enhanced electrical properties.

In one aspect, presented herein is a CNT based electrode and method of making the same. CNT sheets are known to be electrically conducting, transparent, and offer substantial gravimetric strength. Pristine CNT sheets have been shown to foster robust cell migration and neuronal growth, but because CNT sheets are inherently hydrophobic, they aggregate in aqueous environments, minimizing their inherent mechanical and structural advantages.

In one exemplified aspect, the CNT based electrode comprises a microelectrode comprising a substantially inert metal, a first CNT sheet and a second CNT sheet, wherein the first and second CNT sheets are embedded in a collagen film. Collagen is biodegradable and substantially non-immunogenic. As such, CNT sheets embedded on collagen film are not aggregated and maintain their aligned thread in an aqueous environment.

In another aspect, at least a portion of the exposed microelectrode is sandwiched between a pair of CNT sheets embedded on collagen film, creating a CNT flag. The resulting CNT based electrode is flexible with high conductivity, low impedance, high tensile strength, and transparency, with biocompatible and adaptable electromechanical properties defined substantially by the size of the film.

Figure 1A:
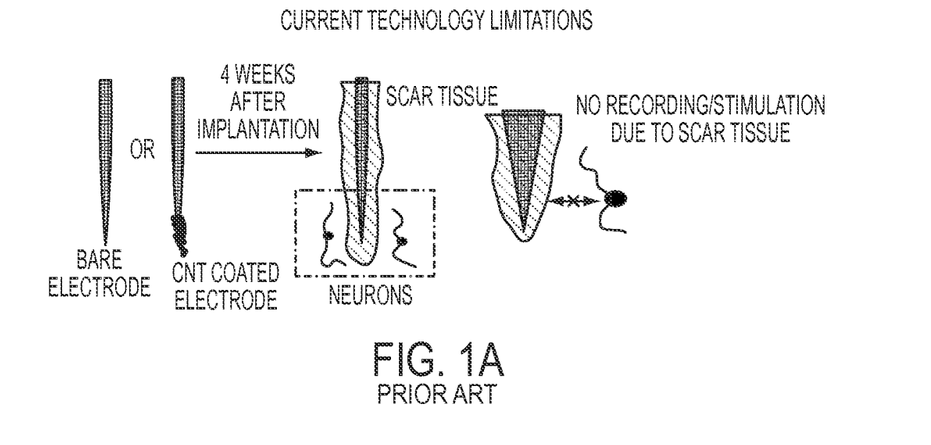
FIG. 1A is a plan view of a bare and CNT coated electrode which illustrates the limitations of the prior art technology by showing scar tissue formation around the electrodes (bare and CNT coated) thereby limiting the electrical performance over time.
Figure 1B:
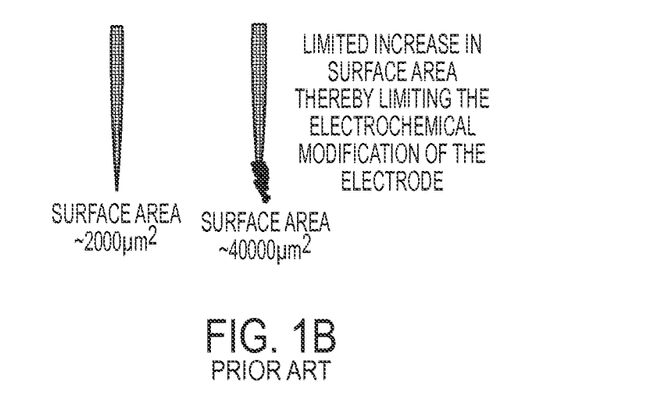
FIG. 1B is a plan view of a bare and CNT coated electrode which illustrates the limited amount of surface area available for modification eventually limiting the enhancement of electrochemical properties
Figure 2A:
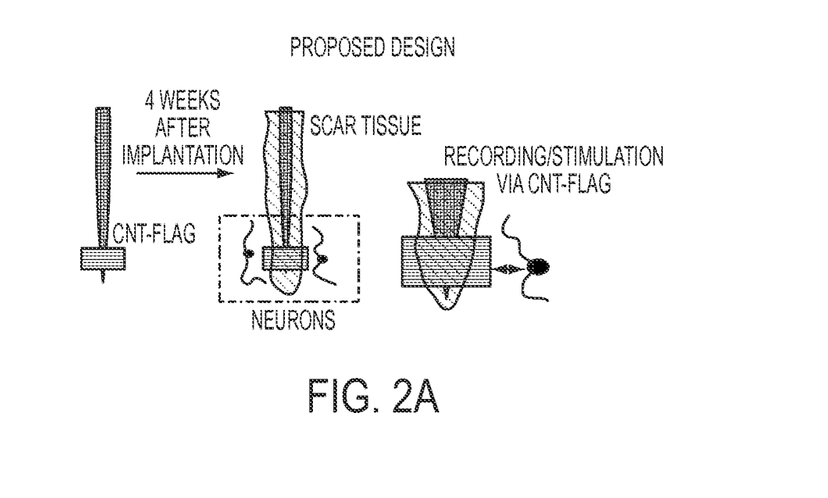
FIG. 2A is a plan view of a CNT based electrode having an electrode sandwiched between two collagen embedded CNT sheets.
Figure 2B:
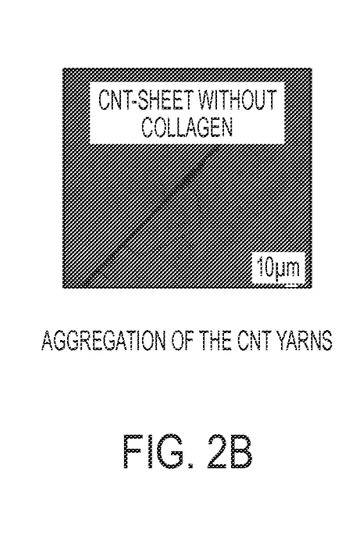
FIG. 2B is a representation of a CNT based electrode without the CNT being embedded on collagen film, showing exposed CNT sheets collapse on the electrode surface, thereby compromising the mechanical and structural functions.
Figure 2C:
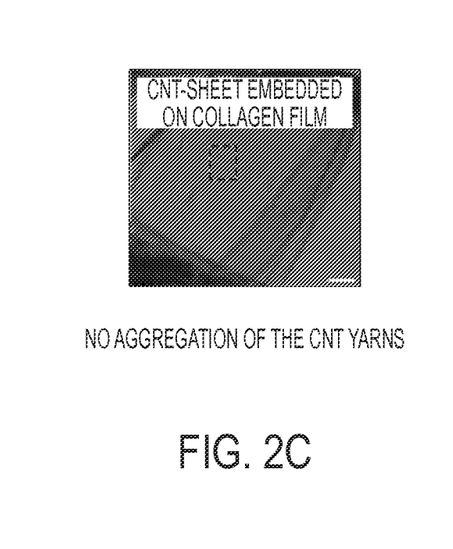
FIGS. 2C and 2D are representations of a CNT based electrode having the CNT embedded on collagen film, showing the retention of the CNT sheets' structure and mechanical properties.
Figure 2D:
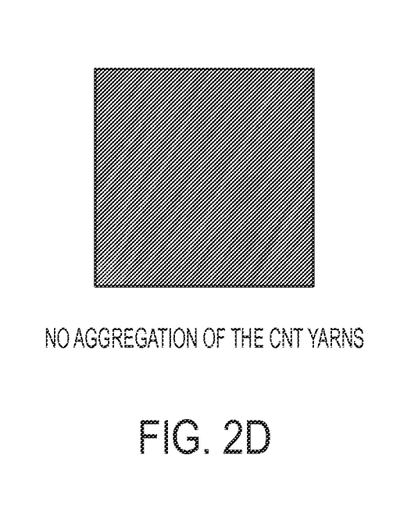

As mentioned herein, scar tissue substantially inhibits the ion distribution between the electrode and the surrounding tissue. As such, in one exemplified aspect, after implantation, the CNT flag extends beyond the scar tissue area to reliably pick up neuronal activities, as shown in FIG. 2A. It is known that the average scar tissue area is approximately 20-80 µm from an implanted microelectrode. Hence, in another aspect, the CNT flag has a width or a length greater than 80 µm. In yet another aspect the CNT flag has a width or a length in the range of 80-400 µm. In still another aspect, the CNT flag has a width or a length approximately 200 µm. It is also contemplated that the CNT flag has a width and a length of equal size.

In one exemplified aspect, the CNT based electrode comprises a plurality of CNT based electrodes in an array. It is contemplated that this aspect can be accomplished using the techniques taught herein, along with modern photolithographic manufacture methods. Photolithography fabrication of electrode arrays is known in the art. The electrode array can be exposed by photoetching both sides of the substrate. In this aspect, the electrode array would be sandwiched by sheets of CNT embedded in collagen, for example.

Experimental Data

One exemplified method for characterizing the electrochemical performance of an implantable microelectrode comprises voltammetry and electrochemical impedance spectroscopy. In one aspect, as shown in FIG. 3, the tip of a tungsten electrode was sandwiched between two CNT sheets that were embedded in collagen. It is contemplated that bonding of the CNT sheets to the microelectrode can be accomplished using medical grade conductive glue, as shown in FIG. 3D, but this method is not limited by this bonding method. In the experiment, USP Class VI approved conductive medical glue was used.

Four samples were tested for impedance variations at a neuronal recording frequency of 500 Hz. Table 1, below, shows that the impedance of the tungsten microelectrode is significantly lowered by the CNT flag.

TABLE 1

| CNT-flag microelectrodes | Pre CNT-flag (k ohm) | After CNT-flag (k ohm) | Reduction factor |
| --- | --- | --- | --- |
| Sample 1 | 1620 | 10 | 162 times |
| Sample 2 | 1450 | 20 | 73 times |

TABLE 1-continued

| CNT-flag microelectrodes | Pre CNT-flag (k ohm) | After CNT-flag (k ohm) | Reduction factor |
|---|---|---|---|
| Sample 3 | 1780 | 40 | 45 times |
| Sample 4 | 1720 | 50 | 34 times |

As can be seen, the impedance was reduced by a factor of between 34 and 162 times that of a sample without a CNT flag.

Figure 4A:
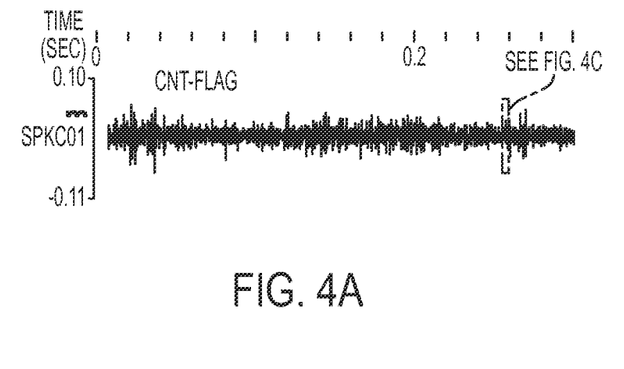
FIG. 4A is a graphical representation of a rat based experiment showing spontaneous neuronal activities (single and compound action potentials) recording from the surface of rat brain using a CNT based microelectrode.
Figure 4B:
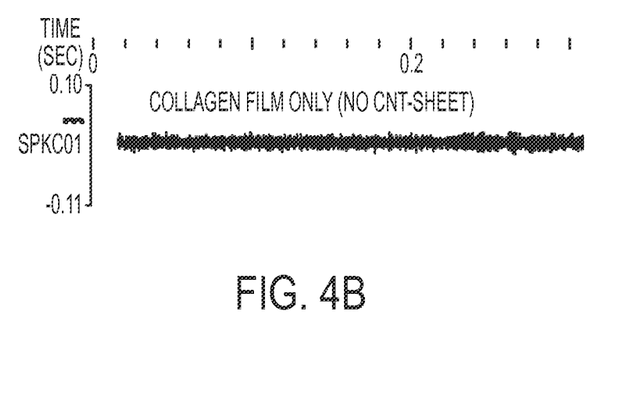
FIG. 4B is a graphical representation of a rat based experiment showing spontaneous neuronal activities (single and compound action potentials) recording from the surface of rat brain using an electrode with collagen film only and no CNT sheet.
Figure 4C:
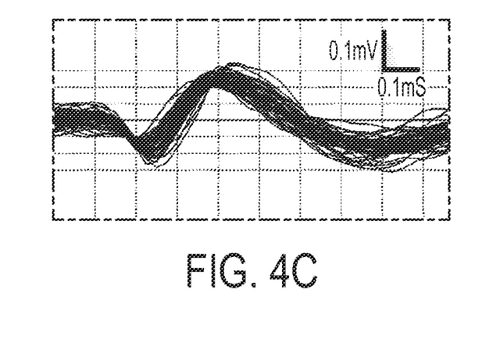
FIG. 4C is an exploded view of the graphical representation of FIG. 4A.
Figure 4D:
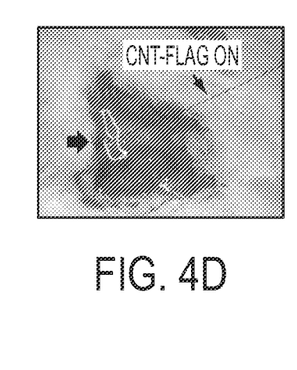
FIG. 4D is a representation of a CNT flag microelectrode placed on the surface of rat brain tissue.

In another experiment, a prototype electrode was deployed to measure spontaneous neuronal recordings from the surface of the rat brain. Single unit spikes were measured from the neuronal traces recorded by the CNT flag electrodes, as shown in FIG. 4A. Conversely, the control with only collagen film attached microelectrode did not show any identifiable single unit spikes, as exemplified in FIG. 4B. These results suggest the potential of the CNT flag electrodes for spike recording with the surface electrodes due to their high sensitivity, which was not possible with the commercially existing surface electrodes. Moreover, the CNT flag electrodes, based on the low impedances observed, could be translated to high signal to noise ratio for electrical signal pick up.

Figure 5:
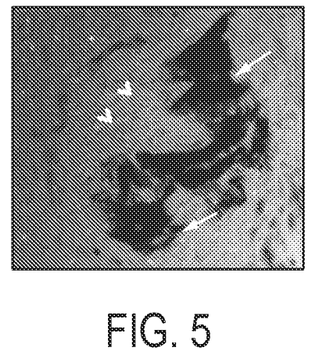
FIG. 5 is a representation of a microphotograph showing the lack of immune response to a CNT-sheet, where macrophages are recruited at the metal microelectrode surface (arrowheads), but not at the CNT-sheet (arrows) in an animal 14 days post implantation in peripheral nerve regeneration model.

As illustrated by FIG. 5, when the microelectrode with the CNT flag were implanted into the rat, a lack of host response was observed for the CNT sheets as compared to the response at the electrode tip. The tissue was harvested after 14 days and further processed for testing immune response (macrophages) via immunofluorescence techniques.

Figure 3A:
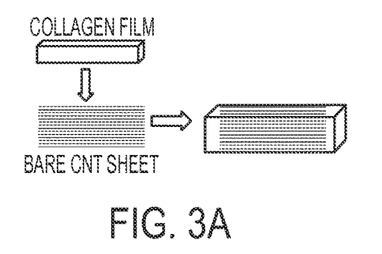
FIG. 3A is a diagrammatical view of a step during prototype fabrication of a CNT based electrode, illustrating collagen film being placed on top of exposed CNT sheets.
Figure 3B:
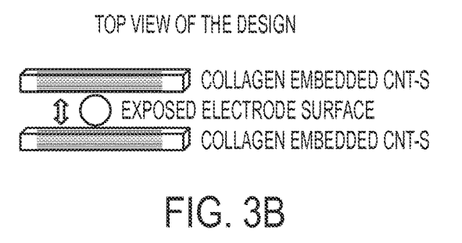
FIG. 3B is a diagrammatical view of a step during prototype fabrication of a CNT based electrode, illustrating an exposed electrode surface being sandwiched between two collagen embedded CNT sheets to form the electrode interface surface.
Figure 3C:
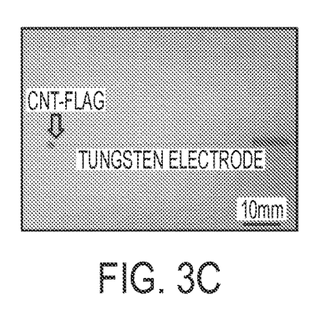
FIG. 3C is a representation of the prototype of FIGS. 3A and 3B.
Figure 3D:
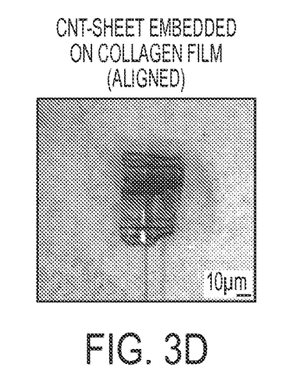
FIG. 3D is a representation of the prototype of FIG. 3C, showing a close up of the electrode tip having a CNT flag.

In one example, A three second 5 volt monophasic pulse was passed through the CNT flag-metal (i.e., tungsten electrode) interface to bond the CNT flag to the metal electrode and to confirm charge transfer through the CNT flag to the metal electrode (FIG. 3B, electric resistance welding setup). Before bonding, resistivity values fluctuated randomly or were read as open circuit values. After bonding, the CNT flag-metal electrode circuit had a resistances of 39.10 kohms+9.99 kohms, which confirms a strong bonding between CNT flag-metal electrode.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. A carbon nanotube based electrode comprising:
a first carbon nanotube sheet and a second carbon nanotube sheet, wherein the first and second carbon nanotube sheets are embedded in a collagen film;
a microelectrode comprising a substantially inert metal partially sandwiched between the first and second carbon nanotube sheets forming a carbon nanotube flag having a width and a length, wherein at least one of the width and length greater than 80 μm.

2. The carbon nanotube based electrode of claim 1, wherein at least one of the width and length of the carbon nanotube flag are in the range of 80-400 μm.

3. The carbon nanotube based electrode of claim 1, wherein at least one of the width and the length of the carbon nanotube flag are approximately 200 μm.

4. The carbon nanotube based electrode of claim 1, wherein the width and the length of the carbon nanotube flag are equal.

5. The carbon nanotube based electrode of claim 1, wherein the carbon nanotube based electrode comprises a plurality of carbon nanotube based electrodes in an array.

6. The carbon nanotube based electrode of claim 5, wherein the array is formed using photolithographic fabrication.

7. The carbon nanotube based electrode of claim 5, wherein the array is formed by photoetching both sides of the carbon nanotube based electrode.

8. A carbon nanotube based electrode comprising:
a first carbon nanotube sheet and a second carbon nanotube sheet, wherein the first carbon nanotube sheet is embedded in collagen and the second carbon nanotube sheet is embedded in collagen; and
a microelectrode having an electrode tip sandwiched between the first carbon nanotube sheet and the second carbon nanotube sheet forming a carbon nanotube flag having a width and a length,
wherein at least one of the width and length greater than 80 μm and wherein the electrode tip is configured for implanting into tissue.

9. The carbon nanotube based electrode of claim 8, wherein at least one of the width and length of the carbon nanotube flag are in the range of 80-400 μm.

10. The carbon nanotube based electrode of claim 8, wherein at least one of the width and the length of the carbon nanotube flag are approximately 200 μm.

11. The carbon nanotube based electrode of claim 8, wherein the width and the length of the carbon nanotube flag are equal.

12. An electrode array comprising a plurality of the carbon nanotube based electrodes of claim 8 in an array.

13. The electrode array of claim 12, wherein the electrode array is formed using photolithographic fabrication.

14. The electrode array of claim 12, wherein the electrode array is formed by photoetching.

15. The electrode array of claim 12, wherein the electrode array is formed by photoetching sides of the electrode array.

16. The carbon nanotube based electrode of claim 8, wherein is microelectrode is made of a substantially inert metal.

17. An electrode array comprising:
a first carbon nanotube sheet and a second carbon nanotube sheet, wherein the first carbon nanotube sheet is embedded in collagen and the second carbon nanotube sheet is embedded in collagen; and
an array of microelectrodes, each microelectrode having an electrode tip sandwiched between the first carbon nanotube sheet and the second carbon nanotube sheet forming a carbon nanotube flag having a width and a length,
wherein at least one of the width and length greater than 80 μm and wherein the electrode tip of each microelectrode is configured for implanting into tissue.

18. The electrode array of claim 17, wherein each microelectrode is made of a substantially inert metal.

19. The electrode array of claim 17, wherein at least one of the width and length of the carbon nanotube flag are in the range of 80-400 μm.

20. The electrode array of claim 17, wherein the electrode array is formed using photolithographic fabrication.

* * * * *